(12) United States Patent
Bain et al.

(10) Patent No.: US 6,786,083 B1
(45) Date of Patent: Sep. 7, 2004

(54) APPARATUS AND METHOD FOR ASSESSMENT OF MATTRESSES

(76) Inventors: Duncan Shirreffs Bain, 531a North Deeside Road, Cults, Aberdeen, Scotland (GB); Martin Ferguson-Pell, 9 The Leys, Chesham Bois, Buckinghamshire (GB); Patrick John Davies, 1 Colthorpe Street, Bondall, Queensland (AU), 4034

(*) Notice: Subject to any disclaimer, the term of this patent is extended or adjusted under 35 U.S.C. 154(b) by 0 days.

(21) Appl. No.: 09/914,767
(22) PCT Filed: Feb. 28, 2000
(86) PCT No.: PCT/GB00/00704
§ 371 (c)(1), (2), (4) Date: Dec. 3, 2001
(87) PCT Pub. No.: WO00/51470
PCT Pub. Date: Sep. 8, 2000

(30) Foreign Application Priority Data

Mar. 5, 1999 (GB) .............................. 9905005

(51) Int. Cl.$^7$ .............................................. G01N 3/40
(52) U.S. Cl. .................................................. 73/78
(58) Field of Search .............................. 73/78, 81, 82, 73/85, 790, 818, 865.3, 805.4

(56) References Cited

U.S. PATENT DOCUMENTS

| 2,436,435 | A | * | 2/1948 | Kent .............................. 73/85 |
| 3,973,432 | A | * | 8/1976 | Toulc'Hoat et al. ........... 73/85 |
| 4,004,457 | A | * | 1/1977 | Eide et al. .................... 73/818 |
| 4,140,008 | A | | 2/1979 | Golembeck et al. |
| 4,304,123 | A | * | 12/1981 | Aschinger et al. |

FOREIGN PATENT DOCUMENTS

| DE | 41 39 697 | 6/1993 |
| WO | 95/10762 | 4/1995 |

* cited by examiner

*Primary Examiner*—Robert Raevis
(74) *Attorney, Agent, or Firm*—Burns, Doane, Swecker & Mathis, L.L.P.

(57) ABSTRACT

Apparatus is described for objectively testing the condition of a support surface such as mattress. The apparatus comprises a frame (8, 21, 22) for extending over the support surface, an indenter (5) mounted on said frame and a load sensor (4) disposed between the indenter and the frame, manually operated means (6) for pressing the indenter into the support surface, displacement measuring means for measuring the movement of the indenter into the support surface and data processing means (7) for analyzing the force applied to the indenter in relation to the displacement of the indenter into the support surface.

13 Claims, 4 Drawing Sheets

APPARATUS AND METHOD FOR ASSESSMENT OF MATTRESSES

This invention relates to apparatus for the assessment of a support surface such as a mattress, so as to determine objectively whether the support surface has worn out.

There are many instances where it is desirable to provide an objective test of the condition of a support surface such as a mattress. For example, it is known that mattresses have a finite life span and that after a period of use, they begin to lose their resilience and this leads to the phenomenon known as "bottoming". This refers to the yielding of the mattress to such an extent that the occupant comes into contact with the hard base of the bed.

In hospitals, such a condition represents a serious hazard which greatly increases the risk of patients developing pressure sores. Since the treatment of pressure sores constitutes substantial expense to the hospital in terms of increased bed occupancy and nursing care, it is desirable to detect deterioration of mattresses at an early stage and dispose of them before the above hazardous condition is reached.

While fatigue of a mattress is related to its age, this is only one factor and masses and other support surfaces cannot be discarded simply on an age basis, since this would lead to disposal of many mattresses which are still in a serviceable condition.

The present established method of determining whether hospital mattresses are in a useable condition is the so-called "nurse fist test". In this test, an experienced operative manually depresses the mattress at three defined points along it's length and subjectively forms an opinion as to the condition of the mattress. However, this subjective test has been shown to suffer from poor repeatability and inter operator reliability.

The present invention, therefore, is directed to the provision of apparatus and method for objectively determining the condition of mattresses and other support surfaces, such as seats and wheelchair cushions.

U.S. Pat. No. 4,140,008 describes apparatus for measuring the firmness of a resilient object, such as a mattress. The apparatus described in this document comprises a platen, which is supported by a frame from a fixed base, and is drawn into the object by a motor.

According to one aspect of the present invention there is provided apparatus for assessing the condition of a person support surface which comprises a frame for extending over the support surface, an indenter mounted on said frame and a load sensor disposed between the indenter and the frame, means for pressing the indenter into the support surface, displacement measuring means for measuring the movement of the indenter into the support surface and data processing means for analysing the force applied to the indenter in relation to the displacement of the indenter into the support surface, characterised in that the apparatus is mobile and includes manually actuated means for pressing the indenter into the support surface.

In general, the apparatus according to the invention will be portable and has a frame which is supported either from the bed base below the mattress, or from a base member which is designed to extend beneath the bed base.

In a preferred form of the invention, the frame is supported in cantilever from one side of the support surface and the indenter is moved downwardly to depress the support surface by pressure applied to a handle by an operator. The frame may include guide means to guide movement of the indenter in an essentially vertical manner into contact with the support surface.

It has been found that a parallelogram frame is suitable to guide movement of the indenter along an essentially vertical path.

In the case of a hospital bed, the frame may be temporarily attached to the support frame of the bed, e.g. by a clamping device, and may be moved to different positions along the bed so as to test the mattress condition in the normal standard points along its length. These generally are one quarter, one half and three quarters of the distance from the head of the bed approximately along a centre line. In the case where the bed has no convenient frame for attachment of the testing apparatus, the frame may be in the form of a C-shaped structure having a base portion adapted to extend beneath the base of the bed, while the upper part of the frame extends over the mattress and enables the indenter to be brought into contact with the surface of the mattress.

The indenter preferably has a curved surface and may, for example, comprise a part of or a complete wheel or sphere.

In use, the indenter is depressed into the mattress until resistance is felt by the operator. A load cell mounted between the indenter and the frame measures the load applied, while displacement of the indenter into the bed is simultaneously measured by a suitable device. In the case where the whole or a part of the frame pivots in cantilever from a support, displacement is conveniently measured by means of a rotary potentiometer or equivalent rotation measurement device which measures pivoting movement of the frame and thus, indirectly, the displacement of the indenter.

Further features of the present invention will become apparent from the accompanying drawings, in which.

Figure 1:
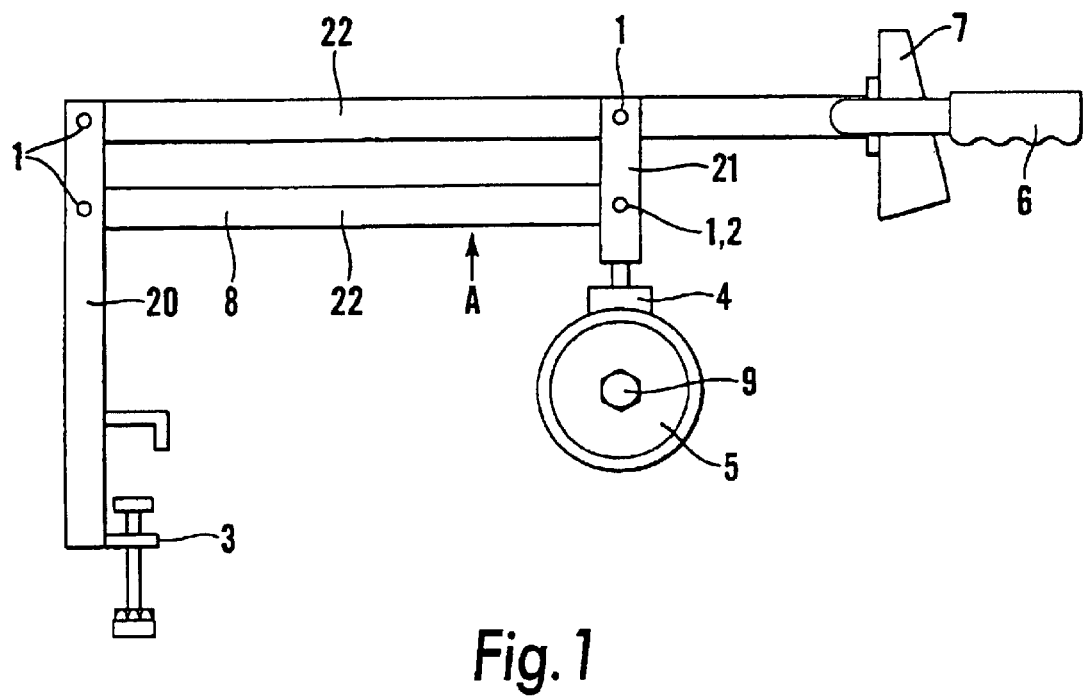
FIG. 1 is a side elevation of one embodiment of the testing apparatus in accordance with the invention.
Figure 2:
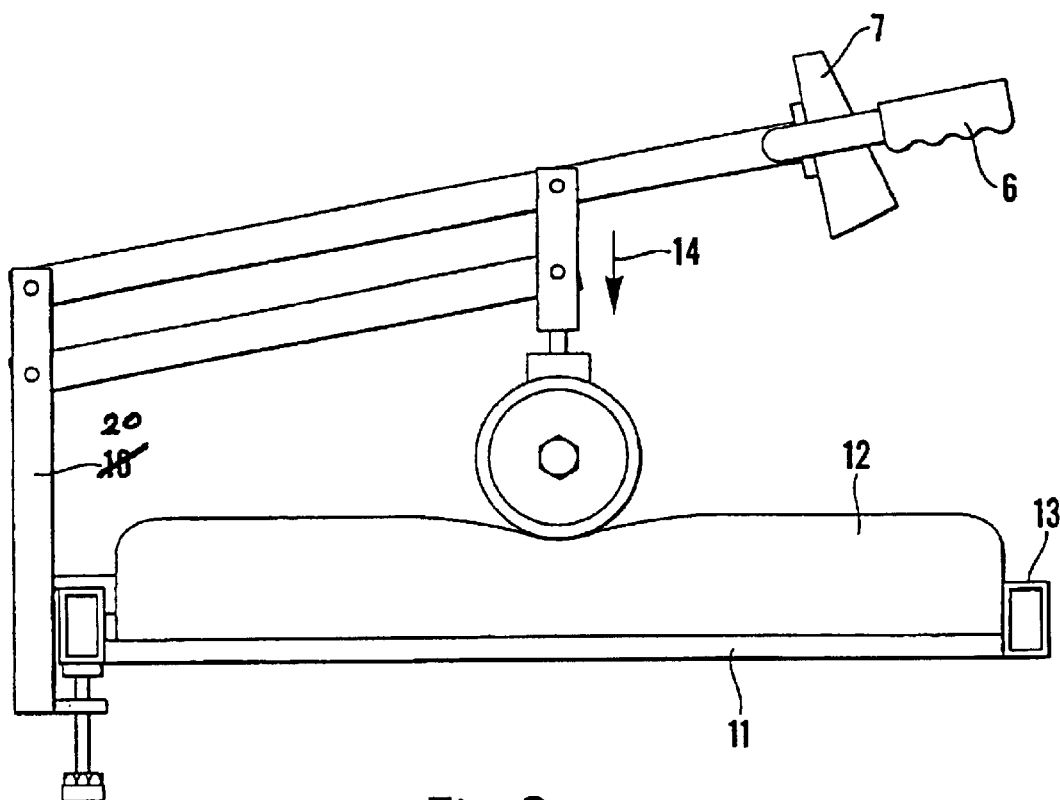
FIG. 2 is a similar view of the apparatus attached to a bed frame in position to test a mattress.
Figure 3:
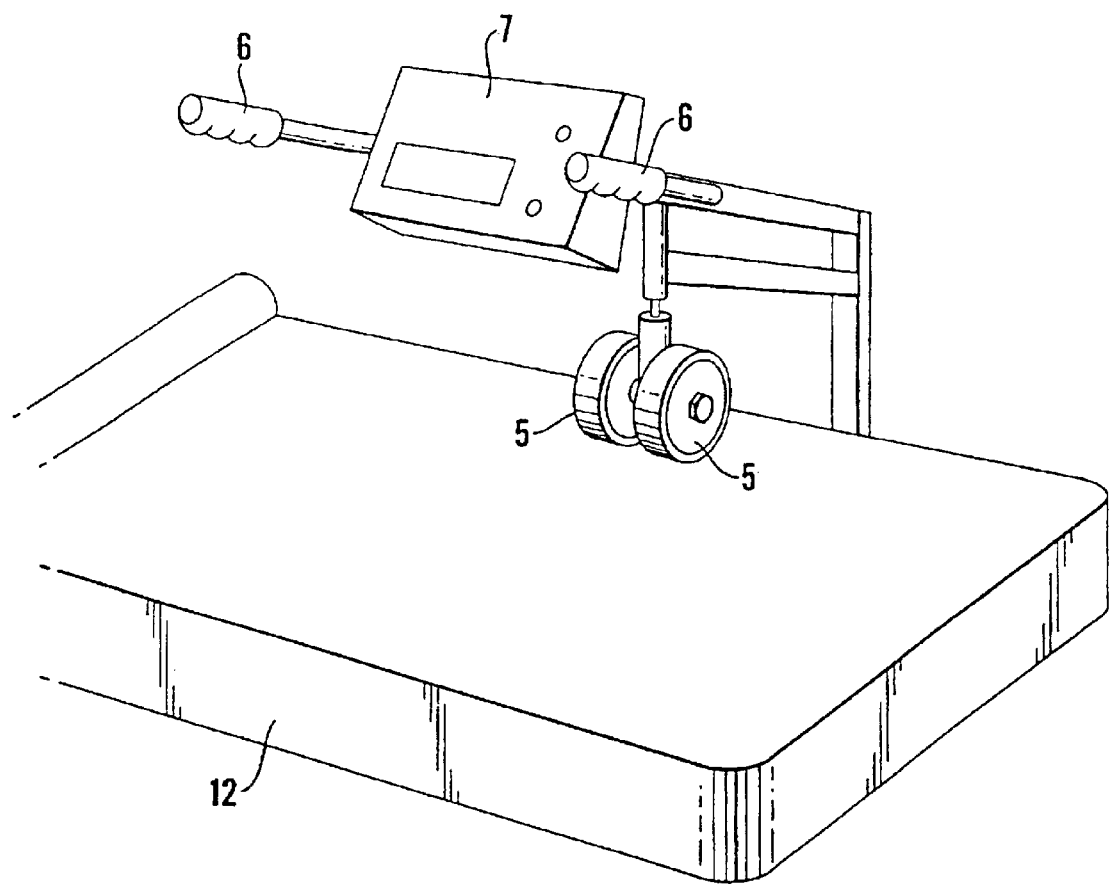
FIG. 3 is a perspective view of the apparatus shown in FIGS. 1 and 2.

Referring to FIGS. 1, 2 and 3, the mattress testing apparatus comprises a frame A including a vertical post (20) for attachment by a clamp (3) to a longitudinal member (13) of a bed frame (11). The vertical post (20) can be rapidly attached to one of the longitudinal members (13) in a desired position by clamp (3) so that the apparatus extends across the bed as shown in FIG. 2. Mounted on the post (20) is a parallelogram structure (8) comprising horizontal and vertical members (22,21) pivotably linked by pivot pins (1).

Incorporated in one of the pivot pins (1) is a rotary potentiometer or other rotary measurement device (2) which measures the angle between the vertical bar (21) and the horizontal bar (22) which, together with the upper part of the post (20) and the other horizontal bar, form the parallelogram structure (8). The upper bar (22) extends in a direction away from the post (20) and is connected to a handle (6) which can be depressed by the operator to force an indenter (5) into contact with the bed in the direction of the arrow (14) shown in FIG. 2.

Mounted between the parallelogram frame (8) and the indenter (5) is a load cell (4). The load cell may be an 'S' or 'C' shaped beam whose distortion under load is transmitted by an electrical signal to a microprocessor.

The indenter wheel (5) is free to rotate about axle (9) which relieves side loads which might be applied to the load cell when the indenter wheel is acting against a horizontal surface. The side loads may otherwise arise from the arc effect of the movement of the linkage. Preferably, a pair of parallel arranged wheels (which may be mounted coaxially) may be employed. This arrangement represents the bony ischial protrusions of a user of the mattress.

A control box (7) is mounted adjacent the handle and contains an analogue to digital converter. Force and displacement information are analysed by a microprocessor contained within the control box (7). Calculations are performed based on the force displacement curve generated by analysing the force displacement data, generated by the rotary potentiometer and the load cell. The results of these calculations are then displayed to the user on an LCD, or other indicating device on the control box.

The control box may also be arranged to report that a proper measurement has been taken and may convert the load displacement data to a single number which rates the condition of the mattresses tested.

The control box may also be arranged to report that a proper measurement has been taken and may convert the load displacement data to a single number which rates the condition of the mattress tested.

Figure 4:
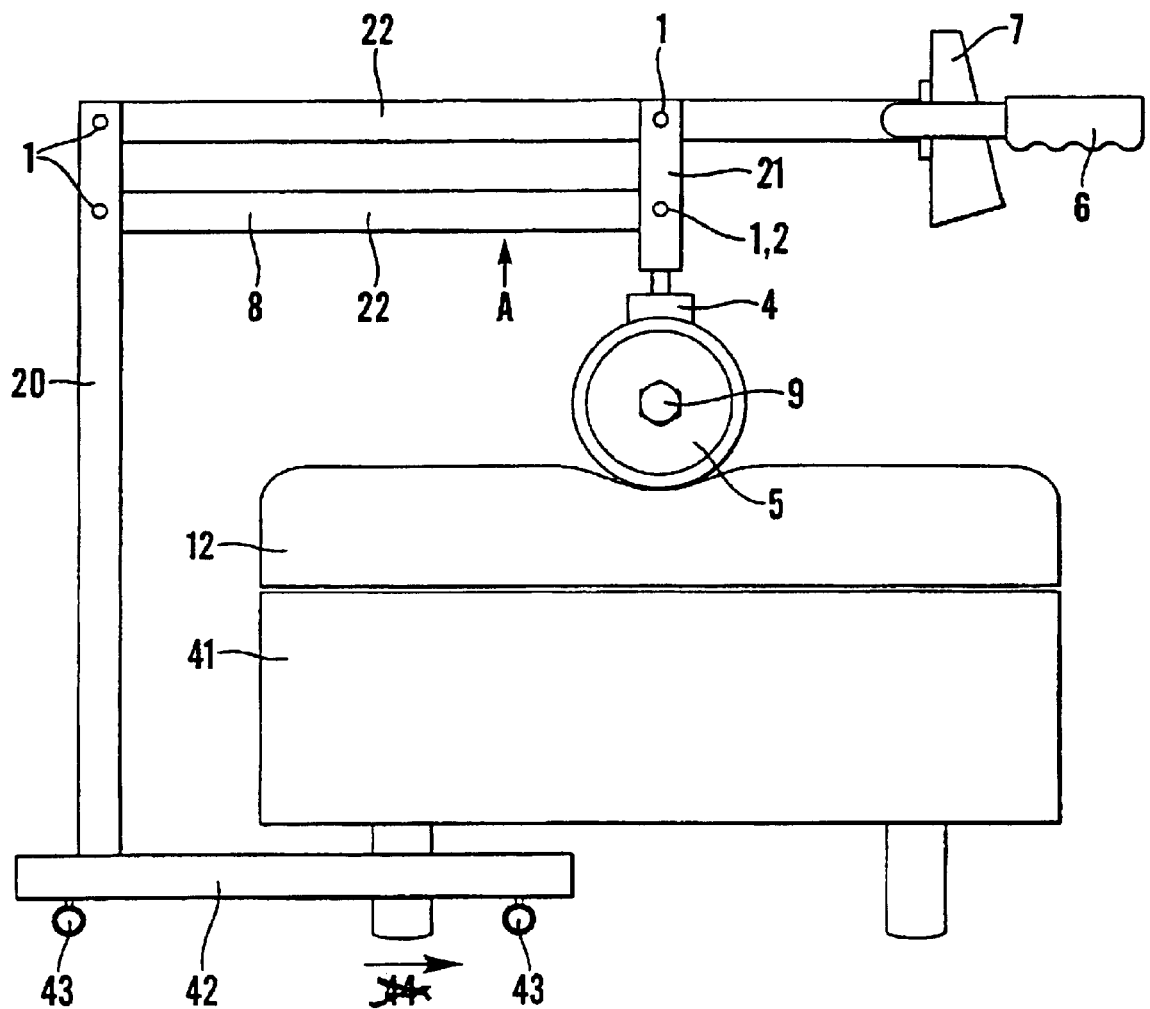
FIG. 4 is a modified apparatus designed for use with beds having no convenient bed frame.

FIG. 4 is a side elevation of a modification of the apparatus shown in FIGS. 1, 2 and 3. The upper part of the apparatus is constructed in the same way as in FIGS. 1, 2 and 4 and the same reference numerals are used to identify equivalent components.

In FIG. 4, the vertical support post (20) is mounted on a platform (42) which may be supported on castors (43). The vertical profile of the platform and castors is low so that it can readily be pushed beneath a bed base (41), which may be of the divan type. In use, the apparatus is pushed beneath the bed base (41) until the post (20) touches the vertical side of the bed base. Handle (6) is depressed to bring the wheel into contact with the surface of the mattress (12) and is pushed into the mattress until maximum resistance is felt and the console (7) indicates that a proper reading has been taken. Data is then processed in the same way as described herein.

Figure 5:
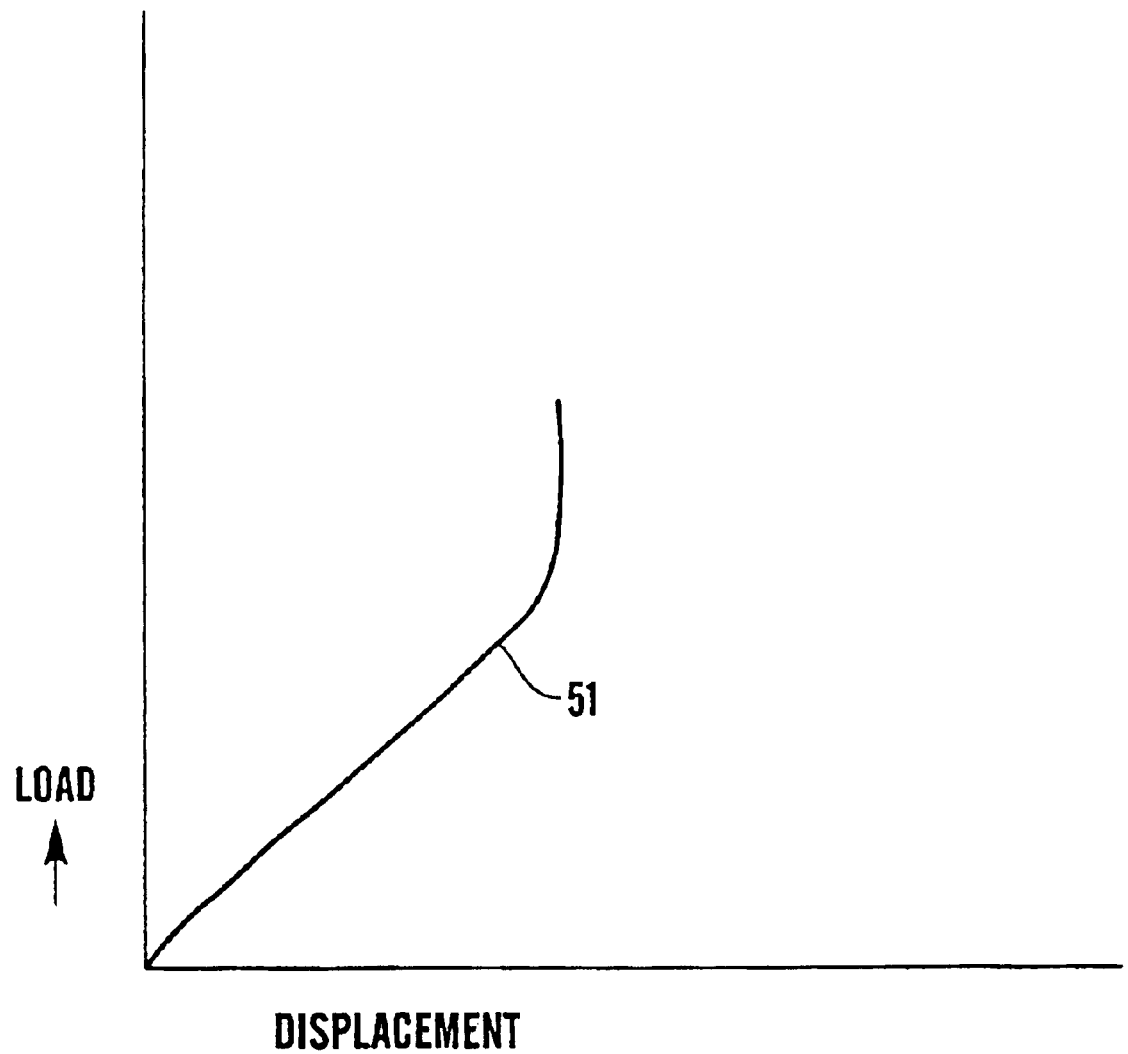
FIG. 5 is a typical load displacement curve obtained by using the apparatus of the invention.

It is important to be able to test the mattresses when they are lying on an existing bed frame so that measurements can be taken in situ. In order to grade mattresses independently of the supporting frame, it is necessary to exclude the displacement of the base when the test is carried out. This is done by assuming that the load displacement curve of the mattress base is a straight line. This part of the data measured can be excluded by carrying out a double differential of the load displacement curve. This results in a figure which indicates the position of the elbow of the curve which is a function of the behaviour of the mattress. A typical load/displacement curve is given in FIG. 5 from which the elbow (51) can clearly be seen.

The microprocessor can also be linked to a device for printing off data about the mattress in the form of a label, which can then be attached to the mattress and re-examined subsequently. The label can be in the form of a printed plastic strip or, in another embodiment, incorporate salient information including the identification of the mattress and the measurement recorded at a previous test. Conveniently, the label may be placed in a pocket in the mattress or cover or attached by pressure sensitive adhesive. If the information is recorded, e.g. on a magnetic strip or on a bar code, it may be machine-readable.

What is claimed is:

1. Apparatus for assessing the condition of a mattress in situ on a bed base which apparatus comprises a frame for extending over the mattress, an indenter mounted on said frame and a load sensor disposed between the indenter and the frame, means for pressing the indenter into the mattress, displacement measuring means for measuring the movement of the indenter into the mattress and data processing means for analyzing the force applied to the indenter in relation to the displacement of the indenter into the mattress, wherein the apparatus includes means for pressing the indenter into the mattress, and the processing means is configured to discriminate and exclude the displacement arising from deflection of the bed base from the displacement arising from deflection of the mattress to thereby identify the load/displacement relationship of the mattress.

2. Apparatus according to claim 1 wherein the frame is supported in cantilever from one side of the mattress.

3. Apparatus according to claim 1 wherein the frame includes means for removable attachment to a bed base for supporting a mattress.

4. Apparatus according to claim 2 wherein the frame is mobile, being supported from a base member having wheels, the base member being adapted to fit beneath a bed base, while said frame is adapted to extend in cantilever over a mattress supported on said bed base.

5. Apparatus according to claim 1, wherein the apparatus has manually operated means comprising a handle for depressing the indenter into the support surface.

6. Apparatus according to claim 1, wherein the indenter comprises a curved surface mounted on said frame.

7. Apparatus according to claim 6, wherein the curved surface comprises a wheel or sphere.

8. Apparatus according to claim 1, wherein the frame comprises a parallelogram linkage.

9. Apparatus for assessing the condition of a person support surface which comprises a frame for extending over the support surface, an indenter mounted on said frame and a load sensor disposed between the indenter and the frame, means for pressing the indenter into the support surface, displacement measuring means for measuring the movement of the indenter into the support surface and data processing means for analyzing the force applied to the indenter in relation to the displacement of the indenter into the support surface, wherein the apparatus is mobile and includes manually actuated means for pressing the indenter into the support surface, wherein said data processing means includes means for assigning an identifying code to a support surface to be tested and for preparing a label bearing said code and data relating to the behavior of the support surface when tested.

10. A method of testing a mattress in situ on a bed base which comprises applying to the surface of the mattress an indenter, depressing the indenter into the mattress, measuring the displacement of the indenter as a function of the load applied to the indenter, constructing a load/displacement curve and discriminating and excluding the displacement arising from deflection of the bed base from the displacement arising from deflection of the mattress to thereby identify the load/displacement relationship of the mattress.

11. Apparatus for assessing the condition of a mattress in situ on a bed base which apparatus comprises a frame for extending over the mattress, an indenter mounted on said frame and a load sensor disposed between the indenter and the frame, means for pressing the indenter into the mattress, displacement measuring means for measuring the movement of the indenter into the mattress and data processing means for analyzing the force applied to the indenter in relation to the displacement of the indenter into the mattress, wherein the apparatus includes means for pressing the indenter into the mattress, wherein the indenter comprises a curved surface mounted on said frame.

12. Apparatus as claimed in claim 11, wherein the curved surface is mounted for rotational movement on said frame.

13. Apparatus for assessing the condition of a mattress in situ on a bed base which apparatus comprises a frame for extending over the mattress, an indenter mounted on said frame and a load sensor disposed between the indenter and the frame, means for pressing the indenter into the mattress, displacement measuring means for measuring the movement of the indenter into the mattress and data processing means for analyzing the force applied to the indenter in relation to the displacement of the indenter into the mattress, wherein the apparatus includes means for pressing the indenter into the mattress, and is mobile by virtue of having wheels, and is readily movable so that a base member of the apparatus extends beneath the bed base.

\* \* \* \* \*